(12) United States Patent
Yuan et al.

(10) Patent No.: US 12,220,293 B2
(45) Date of Patent: Feb. 11, 2025

(54) ROOT CANAL TREATMENT ROBOT AND TREATMENT METHOD

(71) Applicant: PEKING UNIVERSITY SCHOOL OF STOMATOLOGY, Beijing (CN)

(72) Inventors: Fusong Yuan, Beijing (CN); Peijun Lyu, Beijing (CN)

(73) Assignee: PEKING UNIVERSITY SCHOOL OF STOMATOLOGY, Beijing (CN)

( * ) Notice: Subject to any disclaimer, the term of this patent is extended or adjusted under 35 U.S.C. 154(b) by 630 days.

(21) Appl. No.: 17/485,380

(22) Filed: Sep. 25, 2021

(65) Prior Publication Data

US 2022/0008165 A1 Jan. 13, 2022

Related U.S. Application Data

(63) Continuation of application No. PCT/CN2019/086576, filed on May 13, 2019.

(30) Foreign Application Priority Data

Mar. 25, 2019 (CN) .......................... 201910227691.1

(51) Int. Cl.
| | |
|---|---|
| *A61C 5/40* | (2017.01) |
| *A61B 1/07* | (2006.01) |
| *A61B 1/247* | (2006.01) |
| *A61B 34/30* | (2016.01) |
| *A61C 1/00* | (2006.01) |
| *A61C 5/50* | (2017.01) |
| *A61C 5/80* | (2017.01) |

(52) U.S. Cl.
CPC .................. *A61C 5/40* (2017.02); *A61B 1/07* (2013.01); *A61B 1/247* (2013.01); *A61B 34/30* (2016.02); *A61C 1/0061* (2013.01); *A61C 5/50* (2017.02); *A61C 5/80* (2017.02); *A61B 2034/301* (2016.02); *A61B 2034/302* (2016.02)

(58) Field of Classification Search
CPC ......... A61C 1/082; A61C 1/0007; A61C 1/00; A61C 3/02; A61C 9/0046; A61C 5/40; A61B 5/682; A61B 5/4547; A61B 5/0088; A61B 5/80; A61B 5/50; A61B 34/30; A61B 1/07; A61B 1/247; A61B 1/0061; A61B 2034/301; A61B 2034/302
See application file for complete search history.

(56) References Cited

U.S. PATENT DOCUMENTS

| | | | | |
|---|---|---|---|---|
| 2011/0217665 | A1* | 9/2011 | Walsh .................... | G02B 6/262 |
| | | | | 600/478 |
| 2015/0010882 | A1* | 1/2015 | Bergheim .......... | A61C 17/0217 |
| | | | | 433/80 |
| 2018/0368936 | A1* | 12/2018 | Habeb ...................... | A61C 3/02 |

FOREIGN PATENT DOCUMENTS

| | | |
|---|---|---|
| CN | 102178562 A | 9/2011 |
| CN | 104958118 A | 10/2015 |
| CN | 105534612 A | 5/2016 |
| CN | 107088099 A | 8/2017 |
| CN | 108143508 A | 6/2018 |

(Continued)

*Primary Examiner* — Matthew M Nelson

(57) ABSTRACT

A root canal treatment robot and a treatment method using the same. In the robot, a pan tilt, and a working optical fiber are driven by an x-axis movement unit and a y-axis movement unit to move on the x-y plane, and the working optical fiber is further driven by a z-axis movement unit to move along the z-axis, and driven by an a-axis movement unit to rotate around the z-axis.

17 Claims, 8 Drawing Sheets

(56) References Cited

FOREIGN PATENT DOCUMENTS

| | | | |
|---|---|---|---|
| CN | 108430378 | A | 8/2018 |
| CN | 108524024 | A | 9/2018 |
| CN | 109330718 | A | 2/2019 |
| JP | 2014208389 | A | 11/2014 |

* cited by examiner

ROOT CANAL TREATMENT ROBOT AND TREATMENT METHOD

CROSS-REFERENCE TO RELATED APPLICATIONS

This application is a continuation of International Patent Application No. PCT/CN2019/086576, filed on May 13, 2019, which claims the benefit of priority from Chinese Patent Application No. 201910227691.1, filed on Mar. 25, 2019. The content of the aforementioned application, including any intervening amendments thereto, is incorporated herein by reference in its entirety.

TECHNICAL FIELD

This application is related to medical devices, in particular to a root canal treatment robot and a treatment method.

BACKGROUND

The pulp and periapical diseases are generally treated by root canal treatment. Specifically, most of the infections in the root canal are removed by mechanical and chemical methods, and the root canal is filled and the coronal is closed to prevent the periapical disease or to promote the healing of the periapical lesions. The root canal treatment is one of the most basic operating techniques for a dentist. It has been published in the fourth national oral epidemiological survey report that the caries prevalence rates were 62.5%, 41.9%, 89%, 95.6% and 98% for those aged 3-5, 12-15, 35-44, 55-64 and 65-74, respectively, and the DMFT (Decayed, missing and filled teeth) indexes were 3.35, 1.04, 4.54, 8.69 and 13.33 for those aged 3-5, 12-15, 35-44, 55-64 and 65-74, respectively. Thus it can be inferred that currently there are about 4 billion teeth in China that need the root canal treatment.

At present, the entire root canal treatment is generally performed by a manual method in clinic. With regard to the tiny oral cavity space, the root canal is perforated and negotiated by manual tossing and pulling or ultrasonic vibration, or with the help of a hand-held rotating nickel-titanium instrument. It takes about an hour on average to complete the root canal preparation for a three-rooted tooth. Moreover, in the case of the root canal obstruction, it will take one or two hours to negotiate one root canal, which is laborious and inefficient, and will make the dentists suffer from fatigue or even cervical, lumbar and other diseases. More seriously, the improper operation may also cause the fatigue fracture of the instrument and the perforation. Some inexperienced dentists may experience the incomplete treatment, which will easily lead to the secondary infection. Those teeth with severely-calcified root canals, which can not be negotiated by the existing methods, can only be removed.

In addition, the existing method relying on human observation to find the root canal orifice in the pulp cavity is laborious, and has large difficulty in distinguishing, and clinicians rely more on the feeling and touch of their hands. Even though the root canal microscope is adopted nowadays, it is still time-consuming and labor-intensive, and the mirror image deviation may occur in the actual operation. Moreover, the microscope is too expensive to be popularized.

The existing root canal treatment is generally performed through the four-handed operation, that is, one doctor and one nurse for one patient, which brings high labor cost.

SUMMARY

An object of this application is to provide a root canal treatment robot and a treatment method to solve the problems existing in the manual root canal treatment process.

Technical solutions of this application are described as follows.

In a first aspect, this application provides a robot for root canal treatment, comprising:
a main body;
an x-axis movement unit;
a y-axis movement unit;
a pan tilt;
a z-axis movement unit; and
an a-axis movement unit;
wherein the x-axis movement unit, the y-axis movement unit, the pan tilt, the z-axis movement unit and the a-axis movement unit are arranged inside the main body; the pan tilt is in sliding fit with the x-axis movement unit and the y-axis movement unit, and is configured to be driven by the x-axis movement unit and the y-axis movement unit to move in an x-y plane; the z-axis movement unit is arranged on the pan tilt, and is configured to drive an optical fiber for the root canal treatment to move along a z-axis; the optical fiber penetrates through the pan tilt; and the a-axis movement unit is arranged on the pan tilt, and is configured to drive the optical fiber to rotate around the z-axis.

In some embodiments, the optical fiber penetrates through the pan tilt along the z-axis, and a bending direction and a bending degree of the optical fiber are controllable.

In some embodiments, at least one of the z-axis movement unit and the y-axis movement unit comprises a driving part, a transmission part and a guide part; the driving part comprises one of a motor drive system, a pneumatic drive system, an electric drive system, a hydraulic drive system, a gas-hydraulic hybrid drive system, an artificial muscle, and dielectric, magnetic, acoustic, optical, thermal and wind-based polymer, metal, and bio-elastomer drive system; and the transmission part comprises one of a screw transmission part, a wire rope transmission part, a belt transmission part, a chain transmission part, and a gear transmission part.

In some embodiments, the x-axis movement unit comprises an x-axis driving motor, an x-axis screw rod, an x-axis movable sliding rail and an x-axis movable sliding rod; the y-axis movement unit comprises a y-axis driving motor, a y-axis screw rod, a y-axis movable sliding rail and a y-axis movable sliding rod; the x-axis movable sliding rod is in fit with the x-axis screw rod through a first surface, and the y-axis movable sliding rod is in fit with the y-axis screw rod through a second surface; the x-axis movable sliding rod is in fit with a chute of the x-axis movable sliding rail through a third surface, and the y-axis movable sliding rod is in fit with a chute of the y-axis movable sliding rail through a fourth surface; the pan tilt is in fit with a chute on the x-axis movable sliding rod through a fifth surface, and the pan tilt is in fit with a chute on the y-axis movable sliding rod through a sixth surface.

In some embodiments, the z-axis movement unit comprises a z-axis driving motor, a z-axis screw rod, a z-axis movable sliding rail, a z-axis movable sliding rod, an upper platform, a first rolling wheel axle, a second rolling wheel axle, a driving transmission friction wheel, a permanent magnet, a driving optical fiber friction wheel, a first driven transmission friction wheel, a first electromagnetic coil, a first driven optical fiber friction wheel, a second driven transmission friction wheel, a second electromagnetic coil and a second driven optical fiber friction wheel; the upper platform is fixedly connected to the pan tilt; the z-axis driving motor is fixedly connected to the upper platform, and a motor shaft of the z-axis driving motor is in rotating fit with a seventh surface and an eighth surface of the upper platform; the driving transmission friction wheel, the permanent magnet and the driving optical fiber friction wheel are fixedly connected to the motor shaft of the z-axis driving motor; a ninth surface of the first rolling wheel axle is in rotating fit with a tenth surface of the upper platform, and is configured to slide on a eleventh surface of the upper platform; the first driven transmission friction wheel, the first electromagnetic coil and the first driven optical fiber friction wheel are fixedly connected to a first wheel axle tube; the first wheel axle tube is in rotating fit with the first rolling wheel axle, and the first wheel axle tube and the first rolling wheel axle are capable of rotating relative to each other; the first wheel axle tube is restricted by a first snap spring or a first axle sleeve to move along an axial direction of the first rolling wheel axle; a twelfth surface of the first rolling wheel axle is provided with a first torsion spring to separate the first rolling wheel axle from a z-axis driving shaft when the first electromagnetic coil is not energized; a thirteenth surface of the second rolling wheel axle is in rotating fit with an fourteenth surface of the upper platform, and is capable of sliding on a fifteenth surface of the upper platform; the second driven transmission friction wheel, the second electromagnetic coil and the second driven optical fiber friction wheel are fixedly connected to a second wheel axle tube; the second wheel axle tube is in rotating fit with the second rolling wheel axle, and the second wheel axle tube and the second rolling wheel axle are capable of rotating relative to each other; the second wheel axle tube is restricted by a second snap spring or a second axle sleeve to move along an axial direction of the second rolling wheel axle; and a sixteenth surface of the second rolling wheel axle is provided with a second torsion spring to separate the second rolling wheel axle from the z-axis driving shaft when the second electromagnetic coil is not energized.

In some embodiments, the a-axis movement unit comprises an a-axis driving motor, a driving transmission friction wheel, an idler wheel and driven a transmission friction wheel; the driving transmission friction wheel is fixedly connected to a motor shaft of the a-axis driving motor; the idler wheel is in rotating fit with a first shaft provided at a bottom of the pan tilt; and the driven transmission friction wheel is in rotating fit with a second shaft provided at the bottom of the pan tilt, so that a friction wheel transmission is formed by the driving transmission friction wheel, the idler wheel and the driven transmission friction wheel.

In some embodiments, the pan tilt further comprises a Y-shaped optical fiber channel; the y-shaped optical fiber channel is provided at the bottom of the pan tilt, and comprises a first channel for the optical fiber for the root canal treatment and a second channel for an illuminating and imaging optical fiber; and the first channel and the second channel share an outlet, and the second shaft is provided at the outlet.

In some embodiments, the optical fiber for the root canal treatment passes through the first channel, and has a cross-section adapted to the outlet of the first channel in shape.

In some embodiments, the cross-section of the optical fiber for the root canal treatment is non-circular, and the outlet of the first channel is non-circular to be adapted to the cross-section of the optical fiber for the root canal treatment.

In some embodiments, the robot further comprises a gas/liquid circuit unit, where the gas/liquid circuit unit comprises a container for holding a drug and a filling paste, a recycling container, a plurality of electromagnetic valves respectively for controlling communication of individual branches, a power pump and a pipeline.

In some embodiments, the robot further comprises a tooth retainer, where the tooth retainer is configured to be fixed to a dentition of a patient and to fix the main body; and the tooth retainer is provided with a through hole to expose a surgical field.

In a second aspect, this application further provides a root canal treatment method using the above robot, comprising:

fixing the robot relative to a dental hard tissue, and initializing a position of an end of a working optical fiber of the robot according to a coordinate system of the dental hard tissue;

adjusting a height of the end of the working optical fiber relative to a target tooth to complete laser focusing of the working optical fiber; and controlling the working optical fiber to move according to a first preset path, and removing the dental hard tissue above a pulp cavity of the target tooth layer by layer, so as to complete an opening of the pulp cavity of the target tooth.

In some embodiments, the root canal treatment method further comprises: during the step of removing the dental hard tissue of the body above the pulp cavity of the target tooth layer by layer, controlling the robot to deliver cold air to cool a surgical site through a delivery pipeline and to discharge dust generated in a cutting process from the surgical site through a discharge pipeline.

In some embodiments, the root canal treatment method further comprises:

after the opening of the pulp cavity of the target tooth is completed, controlling the working optical fiber of the robot to move in accordance with a second preset path, such that the end of the working optical fiber reaches a vicinity of each root canal in sequence.

In some embodiments, the root canal treatment method further comprises:

after the end of the working optical fiber reaches a vicinity of a root canal, controlling an illuminating and imaging optical fiber of the robot to move along a third preset path; and after the illuminating and imaging optical fiber reaches a designated position, recording a length and a position of the illuminating and imaging optical fiber and withdrawing the illuminating and imaging optical fiber;

controlling the working optical fiber of the robot to move to the designated position according to the recorded length and position of the illuminating and imaging optical fiber; controlling the working optical fiber to generate a controllable bending having the same bending direction and degree with the root canal, and controlling the working optical fiber toy extend into the root canal; and cutting the root canal into a continuous and unobstructed tapered root canal according to a predetermined design during the process of extending the working optical fiber into the root canal.

In some embodiments, the method further comprises:

during the step of cutting the root canal into a continuous and unobstructed tapered root canal according to a predetermined design, controlling the robot to discharge dust generated in the cutting process from a surgical site through a discharge pipeline.

In some embodiments, the root canal treatment method further comprises:

after the end of the working optical fiber reaches a vicinity of a root canal, controlling the robot to quantitatively feed an irrigation and disinfection liquid to a surgical site at a constant pressure through a first delivery pipeline, and discharging the irrigation and disinfection liquid from the surgical site through a discharge pipeline; and controlling the robot to deliver hot air to the surgical site through a second delivery pipeline to dry the root canal and the pulp cavity.

In some embodiments, the root canal treatment method further comprises:

after the end of the working optical fiber reaches a vicinity of a root canal, controlling the robot to discharge air from the surgical site to outside through a discharge pipeline to quantitatively form a negative pressure such that a root canal sealant is sucked to a wall of the root canal through a delivery pipeline, and Gutta Percha is fed into the root canal through the delivery pipeline to complete filling of the root canal.

With respect to the root canal treatment robot and method provided herein, the pan tilt and the optical fiber for the root canal treatment are driven by the x-axis movement unit and the y-axis movement unit to move on the x-y plane, and the optical fiber is further driven by the z-axis movement unit to move along the z-axis, and driven by the a-axis movement unit to rotate around the z-axis, which implements the four-degree-of-freedom control of the treating optical fiber, diversifying the movement of the optical fiber for the root canal treatment. The disclosure solves the problem in the manual root canal treatment and reduces the labor cost for the root canal treatment.

BRIEF DESCRIPTION OF THE DRAWINGS

The drawings described herein are intended to facilitate the understanding of the application. Presented in the drawings are merely some embodiments of the disclosure, which are merely illustrative and are not intended to limit the disclosure.

DETAILED DESCRIPTION OF EMBODIMENTS

The disclosure will be described in detail below with reference to the embodiments and accompanying drawings to make the objectives, technical solutions, and advantages clearer. It should be understood that these embodiments are only illustrative of the application, and are not intended to limit the application. For those skilled in the art, the present application can be implemented without some of these specific details. The following description of the embodiments is only to promote the understanding of the present application.

It should be noted that as used herein, relational terms such as "first" and "second" are merely intended to distinguish one entity or operation from another entity or operation, and do not necessarily require or imply such an actual relationship or order between these entities or operations. Furthermore, the term "comprise", "include", "contain" or any other variations are intended to encompass a non-exclusive inclusion, such that a process, method, article, or instrument not only includes those listed elements, but also includes those that are not clearly listed, or those elements that are inherent to such a process, method, article, or instrument. If there are no more restrictions, the elements defined by the sentence "comprising . . . " do not exclude the existence of other identical elements in the process, method, article, or instrument comprising the elements.

Figure 1:
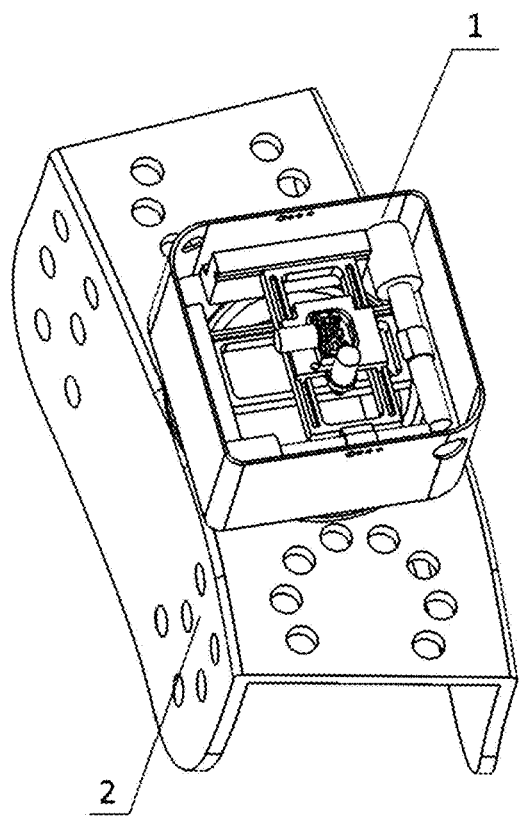
FIG. 1 is an overall structural view of a root canal treatment robot system according to an embodiment of the present application.
Figure 2A:
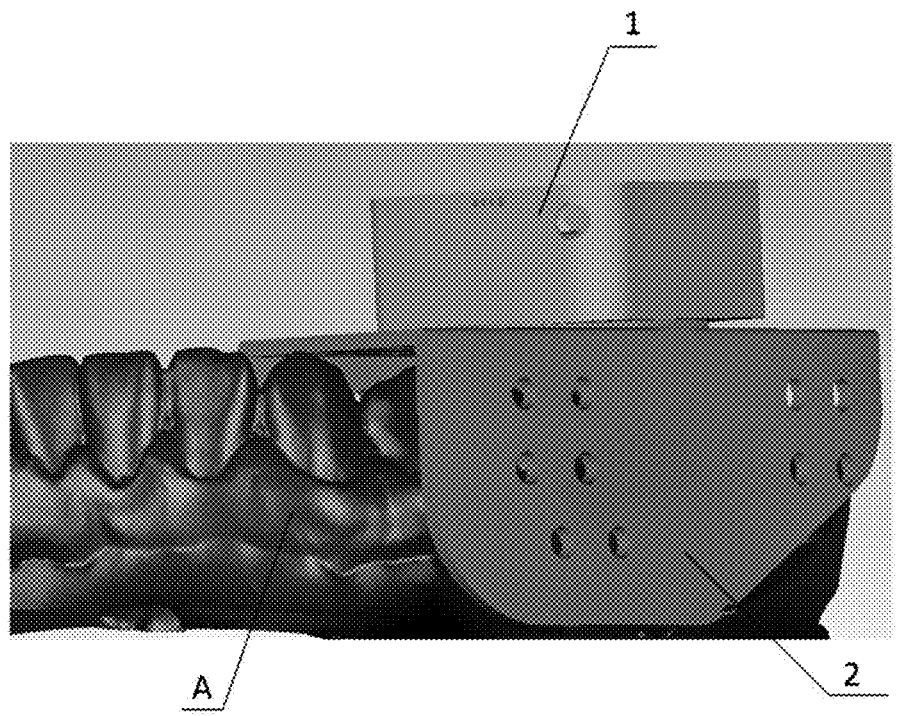
FIG. 2a is a schematic view of the root canal treatment robot system according to an embodiment of the present application in use.
Figure 2B:
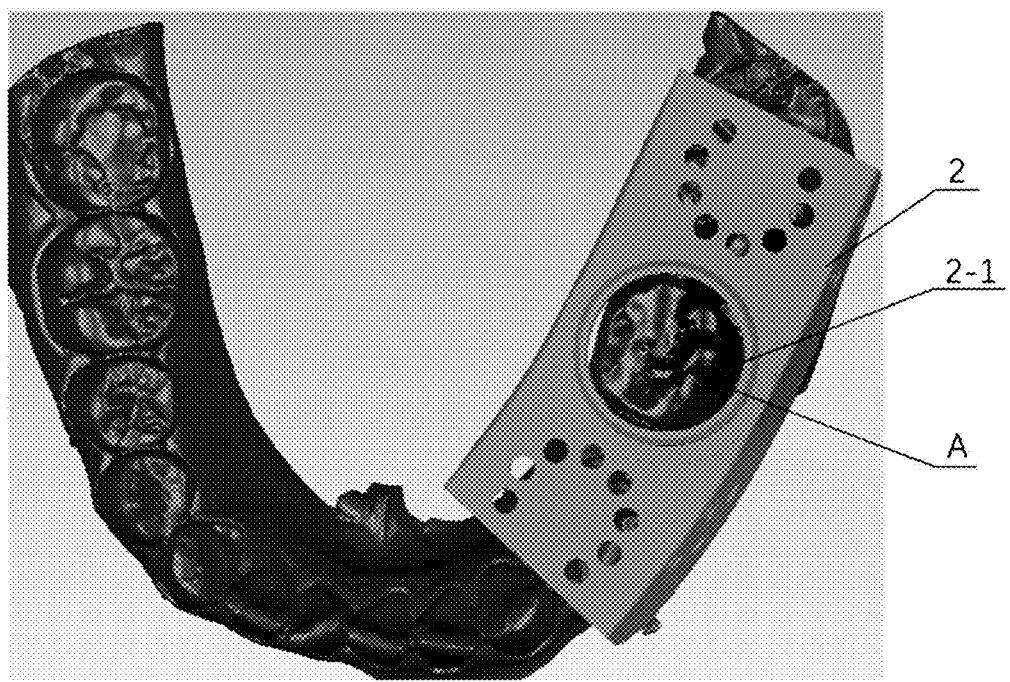
FIG. 2b is a schematic view of a tooth retainer according to an embodiment of the present application in use.

The disclosure provides a robot system for the root canal treatment, where FIG. 1 illustrates an overall structural of the robot system according to an embodiment of the present application; and FIG. 2a shows the robot system according to an embodiment of the present application in use. As shown in FIGS. 1 and 2a, the robot system includes a robot 1 for the root canal treatment. In some embodiments, the robot system further includes a tooth retainer 2 used in conjunction with the robot 1. FIG. 2b schematically shows the operation status of the tooth retainer 2 according to an embodiment of the present application.

In FIG. 2a, A is the three-dimensional data of the dentition. In the practical application, the tooth retainer 2 is fixed to the patient's dentition by a retaining material (such as silicone rubber), and the target tooth (requiring the root canal treatment) is exposed to the surgical field 2-1, then the robot 1 for the root canal treatment controls the working laser to treat root canals of the target tooth according to a pre-designed procedure and path.

Figure 3:
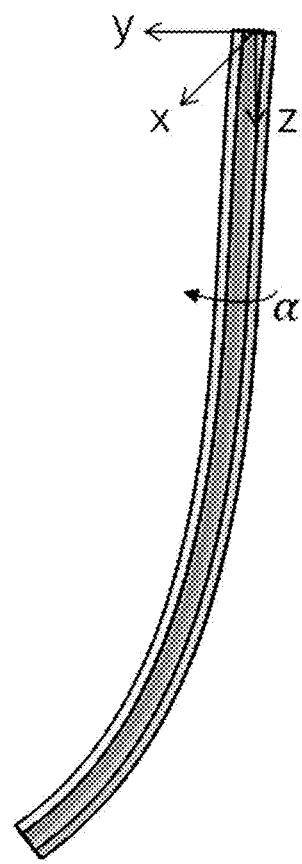
FIG. 3 is a schematic view showing degrees of freedom of an optical fiber for the root canal treatment according to an embodiment of the present application.
Figure 4:
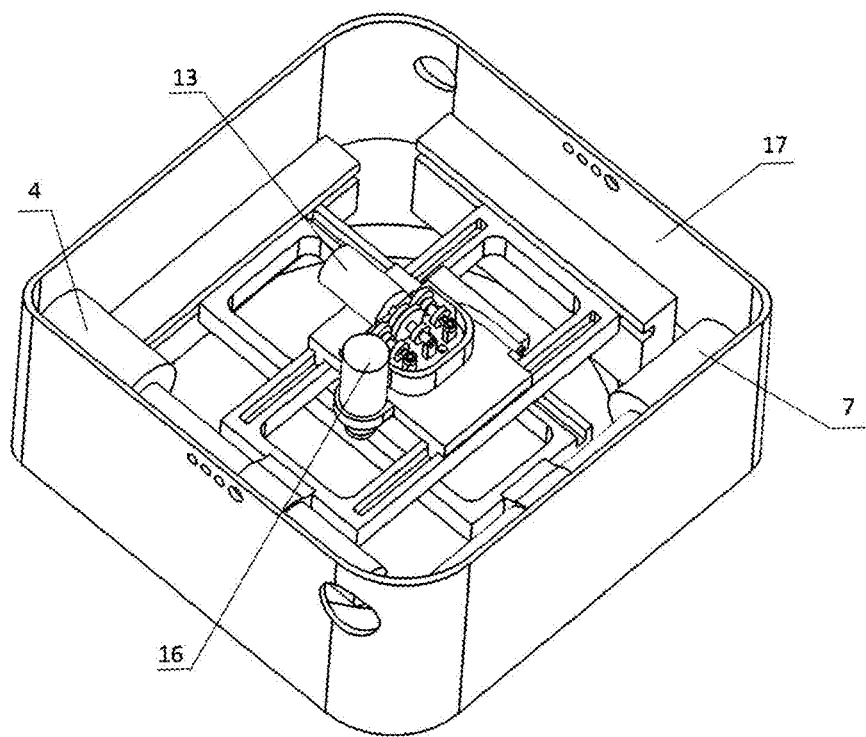
FIG. 4 shows an overall structure of a root canal treatment robot according to an embodiment of the present application.

The robot 1 is mainly used to control the four degrees of freedom of the optical fiber for the root canal treatment (referred to as working optical fiber below), including three translational degrees of freedom, namely translations along x, y, and z directions perpendicular to each other, and one rotational degree of freedom, namely the rotation around the z-axis (a-axis rotation), as shown in FIG. 3. The overall structure of the robot 1 is shown in FIG. 4, including an x-axis driving motor 4, a y-axis driving motor 7, a z-axis driving motor 13, an a-axis driving motor 16 and other components to enable the four-degree-of-freedom movement of the working optical fiber. In practice, in addition to the motor, the four-degree-of-freedom movement of the working optical fiber can also be enabled based on hydraulic pressure, air pressure, artificial muscle and dielectric, thermal or magnetic elastomer materials.

Figure 5A:
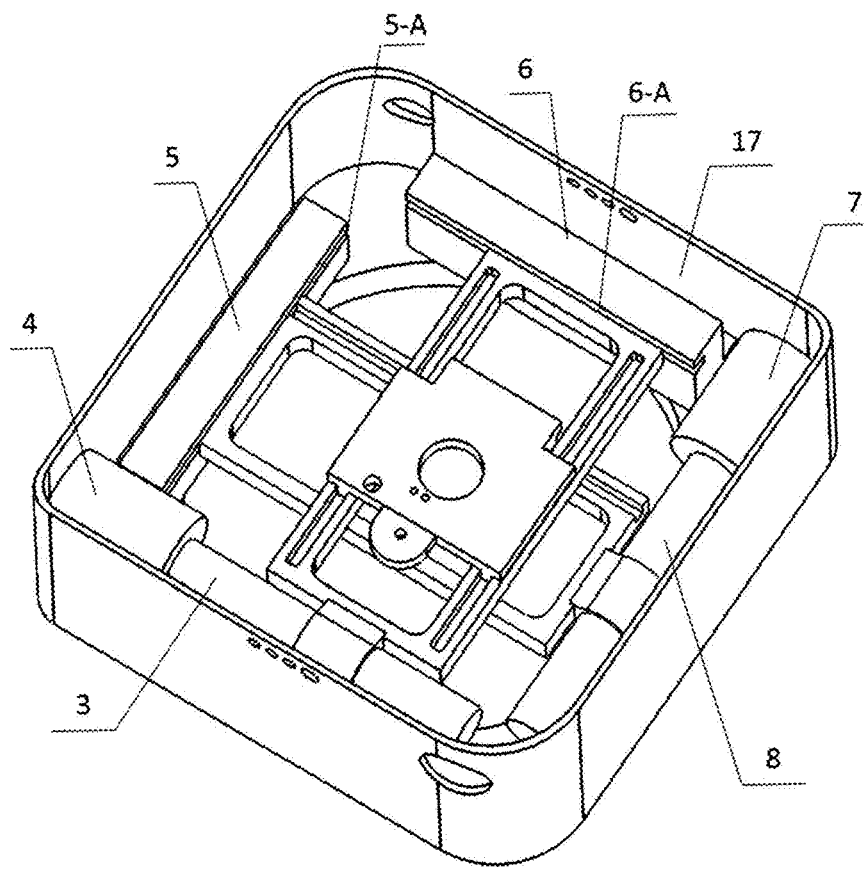
FIGS. 5a and 5b are schematic views of an x-axis movement unit and a y-axis movement unit of the root canal treatment robot according to an embodiment of the present application.
Figure 5B:
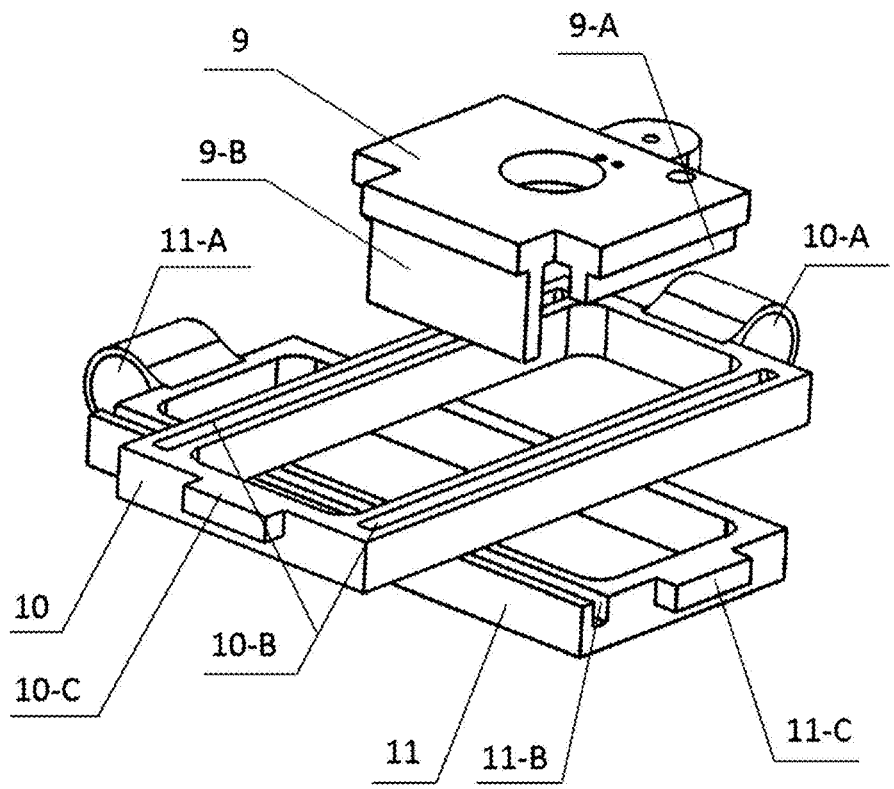

FIGS. 5a and 5b show an x-y movement unit of the robot, including the x-axis driving motor 4, an x-axis screw rod 3, an x-axis movable sliding rail 6, an x-axis movable sliding rod 10, the y-axis driving motor 7, a y-axis screw rod 8, a y-axis movable sliding rail 5, a y-axis movable sliding rod 11 and a pan tilt 9. The x-axis driving motor 4, the y-axis driving motor 7, the x-axis movable sliding rail 6 and the y-axis movable sliding rail 5 can be fixed to the main body 17 by screw fastening, welding, riveting or adhesive bonding. The x-axis movable sliding rod 10 fits with the x-axis screw rod 3 through a first surface 10-A, and the y-axis movable sliding rod 11 fits with the y-axis screw rod 8 through a second surface 11-A. The x-axis movable sliding rod 10 fits with a chute 6-A of the x-axis movable sliding rail 6 through a third surface 10-C, and the y-axis movable sliding rod 11 fits with a chute 5-A of the y-axis movable sliding rail 5 through a fourth surface 11-C. The pan tilt 9 fits with a chute 10-B of the x-axis movable sliding rod 10 through a fifth surface 9-A, and fits with a chute 11-B of the y-axis movable sliding rod 11 through a sixth surface 9-B. Through the above design, the x-axis driving motor 4 drives the x-axis screw rod 3 to rotate, and the x-axis screw rod 3 further drives the x-axis movable sliding rod 10 to slide along the x-axis relative to the x-axis movable sliding rail 6, thereby driving the pan tilt 9 to move along the x-axis. Similarly, the y-axis driving motor 7 drives the y-axis screw rod 8 to rotate, and the y-axis screw rod 8 further drives the y-axis movable sliding rod 11 to slide along the y-axis relative to the y-axis movable sliding rail 5, thereby driving the pan tilt 9 to move along the y-axis. In practice, in addition to the screw transmission, the wire rope transmission, belt transmission, chain transmission or gear transmission is also feasible.

Figure 6:
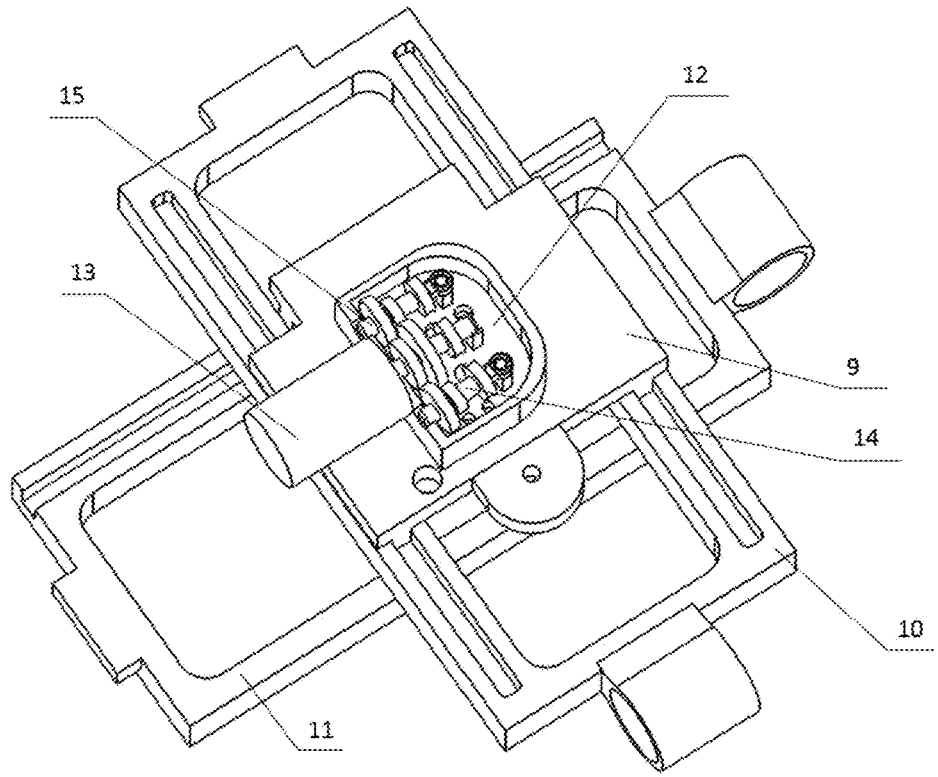
FIG. 6 is a schematic view of a z-axis movement unit of the root canal treatment robot according to an embodiment of the present application.
Figure 7A:
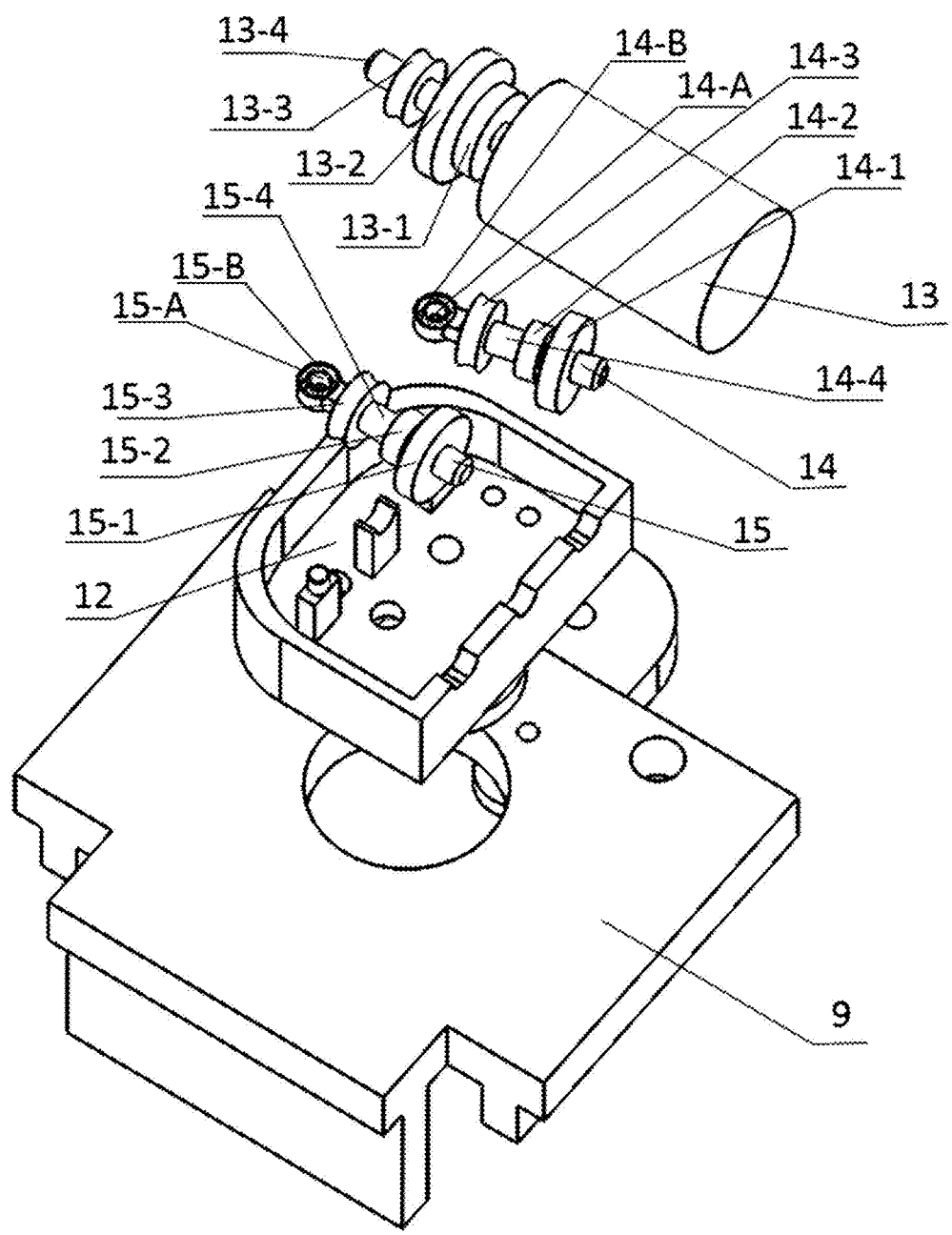
FIGS. 7a and 7b are exploded views of the z-axis movement unit of the root canal treatment robot according to an embodiment of the present application.
Figure 7B:
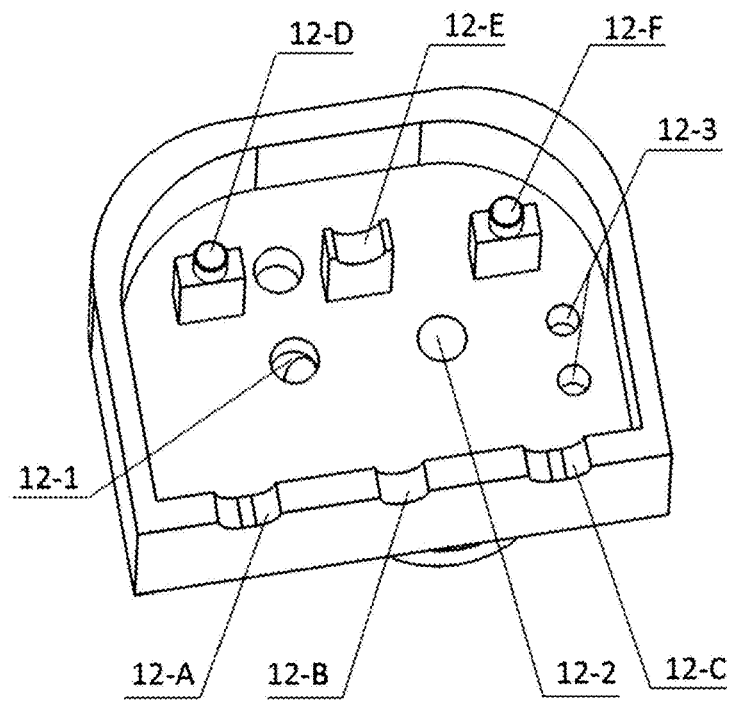

FIG. 6 shows a z-axis movement unit of the robot 1, including an upper platform 12, a z-axis driving motor 13, a first rolling wheel axle 14, a second rolling wheel axle 15, and their individual components. FIGS. 7a and 7b are exploded views of the z-axis movement unit of the robot 1 for the root canal treatment.

The upper platform 12 is fixedly connected to the pan tilt 9 by a screw 12-3. The z-axis driving motor 13 is fixedly connected to the upper platform 12 by a flange and a screw, and a motor shaft 13-4 of the z-axis driving motor 13 is in rotating fit with a seventh surface 12-B and an eighth surface 12-E of the upper platform 12. A driving transmission friction wheel 13-1, a permanent magnet 13-2, and a driving optical fiber friction wheel 13-3 are fixedly connected to the motor shaft 13-4 of the z-axis driving motor 13, so that they can be driven by the z-axis driving motor 13 to rotate together. A ninth surface 14-A of the first rolling wheel axle 14 is in rotation fit with a tenth surface 12-F of the upper platform 12, and is capable of sliding on an eleventh surface 12-C of the upper platform 12. A first driven transmission friction wheel 14-1, a first electromagnetic coil 14-2, a first driven optical fiber friction wheel 14-3 are fixedly connected to a first wheel axle tube 14-4. The first wheel axle tube 14-4 is in rotating fit with the first rolling wheel axle 14, both of which can rotate relative to each other. Meanwhile, the first wheel axle tube 14-4 is limited by a snap spring or an axle sleeve to move along an axial direction of the first rolling wheel axle 14. A twelfth surface 14-B of the first rolling wheel axle 14 is provided with a torsion spring to separate the first rolling wheel axle 14 from a z-axis driving shaft in the initial state (the first electromagnetic coil 14-2 is not energized). A thirteenth surface 15-A of the second rolling wheel axle 15 is in rotating fit with a fourteenth surface 12-D of the upper platform 12, and is capable of sliding on a fifteenth surface 12-A of the upper platform 12. A second driven transmission friction wheel 15-1, a second electromagnetic coil 15-2 and a second driven optical fiber friction wheel 15-3 are fixedly connected to the second wheel axle tube 15-4, and the second wheel axle tube 15-4 is in rotating fit with the second rolling wheel axle 15, both of which can rotate relative to each other. The second wheel axle tube 15-4 is limited by a snap spring or an axle sleeve to move along an axial direction of the second rolling wheel axle 15. A sixteenth surface 15-B of the second rolling wheel axle 15 is provided with a torsion spring to separate the second rolling wheel axle 15 from the z-axis driving shaft in the initial state (the second electromagnetic coil 15-2 is not energized).

The implementation process that the robot drives the illuminating and imaging optical fiber 12-1 and the working optical fiber 12-2 to move along the z-axis is described as follows. As mentioned above, in the initial working state, the first rolling wheel axle 14 and the second rolling wheel axel 15 are separated from the motor shaft of the z-axis driving motor under the action of the torsion spring, and if it is required to drive the working optical fiber to move along the z-axis, the first electromagnetic coil 14-2 is needed to be energized to generate a magnetic field that attracts the permanent magnet 13-2. As a consequence, the permanent magnet 13-2 attracts the first rolling wheel axle 14 to rotate relative to the tenth surface 12-F, so that the first driven transmission friction wheel 14-1 contacts the driving transmission friction wheel 13-1, and simultaneously, the working optical fiber 12-2 is clamped by the driving optical fiber friction wheel 13-3 and the first driven optical fiber friction wheel 14-3. At this time, the z-axis driving motor 13 rotates to drive the first rolling wheel axle 14 to rotate by friction wheel transmission and drive the working optical fiber 12-2 to move along the z-axis. If it is required to drive the illuminating and imaging optical fiber 12-1 to move along the z-axis, the second electromagnetic coil 15-2 is energized to generate a magnetic field that attracts the permanent magnet 13-2. As a consequence, the permanent magnet 13-2 attracts the second rolling wheel axle 15 to rotate relative to the fourteenth surface 12-D, so that the second driven transmission friction wheel 15-1 is in contact with the driving transmission friction wheel 13-1, and simultaneously, the illuminating and imaging optical fiber 12-1 is clamped by the driving optical fiber friction wheel 13-3 and the second driven optical fiber friction wheel 15-3. In this case, the z-axis driving motor rotates to drive the second rolling wheel axle 15 to rotate by the friction wheel transmission and drive the illuminating and imaging optical fiber 12-1 to move along the z-axis direction. The first electromagnetic coil 14-2 and the second electromagnetic coil 15-2 cannot be energized at the same time, namely, only one of the working optical fiber 12-2 and the illuminating and imaging optical fiber 12-1 can be driven to move along the z-axis at the same time.

Figure 8A:
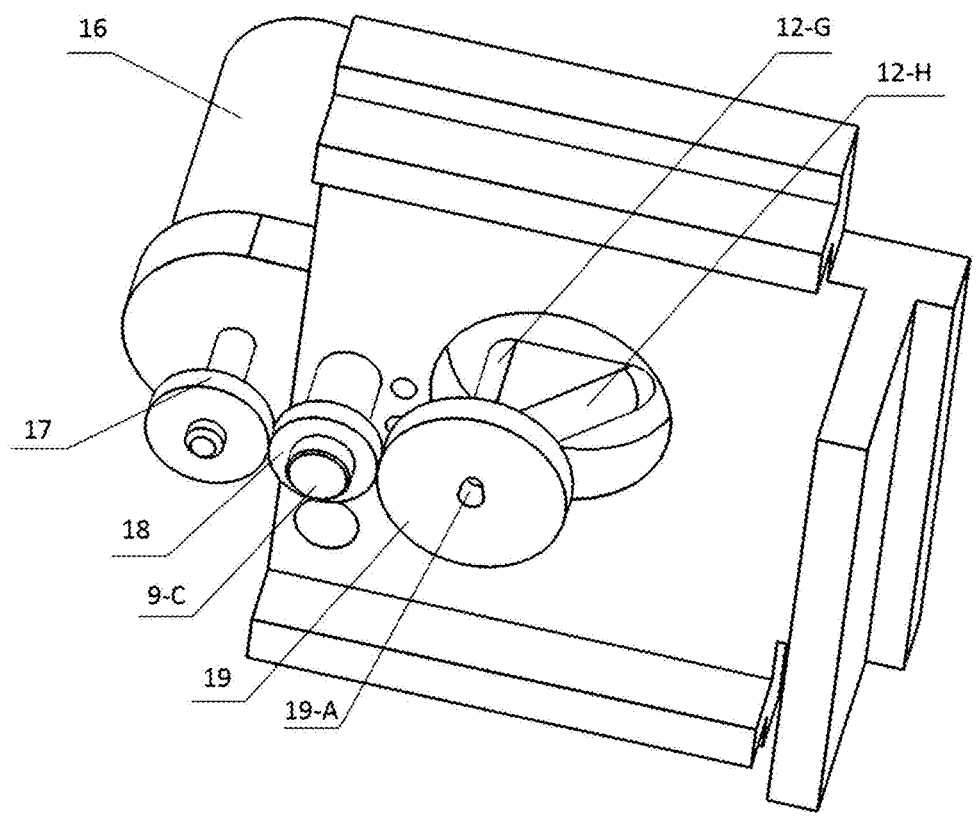
FIGS. 8a and 8b are schematic views of an a-axis movement unit of the root canal treatment robot according to an embodiment of the present application.
Figure 8B:
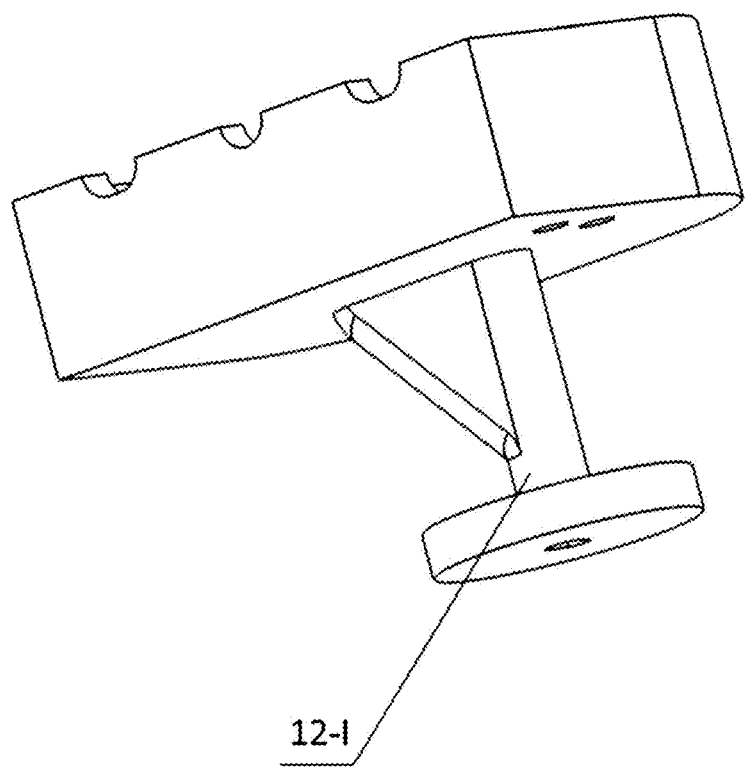
Figure 9:
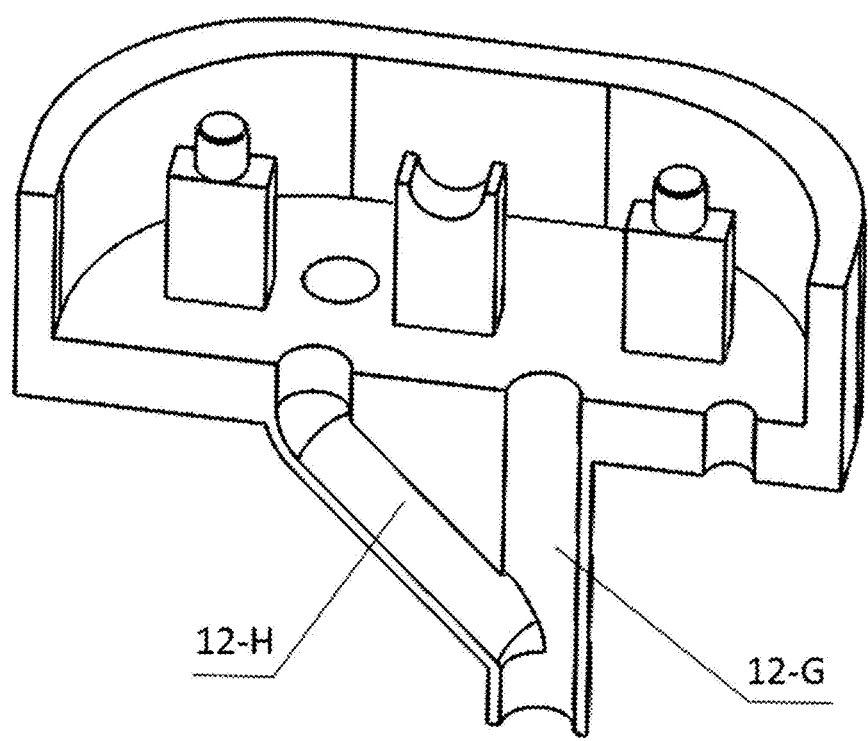
FIG. 9 is a schematic diagram of a Y-shaped optical fiber channel according to an embodiment of the present application.

FIGS. 8a and 8b show the a-axis movement unit of the robot, including an a-axis driving motor 16, a driving transmission friction wheel 17, an idler wheel 18, and a driven transmission friction wheel 19. The driving transmission friction wheel 17 is fixedly connected to a motor shaft of the a-axis driving motor 16. The idler wheel 18 is in rotating fit with a first shaft 9-C arranged at a bottom of the pan tilt 9, and the driven transmission friction wheel 19 is in rotating fit with a second shaft 12-I arranged at the bottom of the pan tilt 9. The driving transmission friction wheel 17, the idler wheel 18 and the driven transmission wheel 19 together form the friction wheel transmission. The working optical fiber 12-2 passes through a pipe 12-G and extends out from the outlet 19-A, and the illuminating and imaging optical fiber 12-1 passes through the pipe 12-H and extends out from the outlet 19-A. The Y-shaped optical fiber channel is shown in FIG. 9. It should be noted that the Y-shaped channel can be any channel that has two inlets and shares one outlet. For example, the Y-shaped channel can be a T-shaped channel or other Y-shaped channels.

The rotation of the working optical fiber 12-2 around the z-axis is performed as follows. The working optical fiber 12-2 is driven by the z-axis movement unit to extend out from the outlet 19-A of the pipe 12-G, where the working optical fiber 12-2 of the micro-robot for the root canal treatment may have a circular or non-circular cross section, preferably a non-circular cross section, such as an elliptical, dumbbell-shaped and polygonal cross section. Moreover, the cross section of the working optical fiber 12-2 is matched with the outlet 19-A in shape, so that when the a-axis driving motor drives the driven transmission friction wheel 19 to rotate through the friction wheel transmission, the working optical fiber 12-2 will be driven to rotate around the z-axis.

In practice, in order to make the working optical fiber 12-2 reach the designated position precisely, it is feasible to move the illuminating and imaging optical fiber 12-1 to the vicinity of the target root canal orifice through the z-axis movement unit to determine the position of the root canal orifice by imaging recognition. Then the z-axis movement unit pulls out the illuminating and imaging optical fiber 12-1, and moves the working optical fiber 12-2 to the determined position of the root canal orifice through the Y-shaped channel, and to be inserted into the target root canal for treatment.

It can be seen that the above Y-shaped channel makes the working optical fiber 12-2 and the illuminating and imaging optical fiber 12-1 be located in the same coordinate system, and further in combination with the xyza-axis motor feedback system, the position of the working optical fiber 12-2 can be precisely determined. In the practical application, the working optical fiber 12-2 and the illuminating and imaging optical fiber 12-1 can be changed from the horizontal (vertical) direction to the vertical (horizontal) direction by rotating the suspension disk, which facilitates the a-axis driving motor 16 to drive the 360-degree rotation of the optical fiber.

Figure 10:
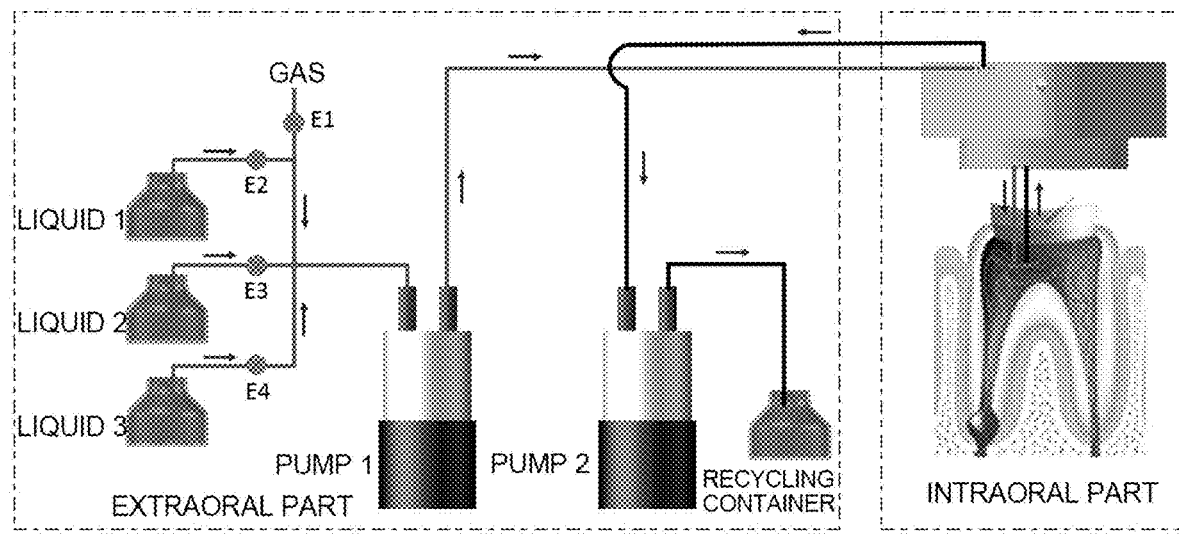
FIG. 10 schematically illustrates a gas/liquid circuit unit of the root canal treatment robot system in accordance with an embodiment of the present application.
Figure 11:
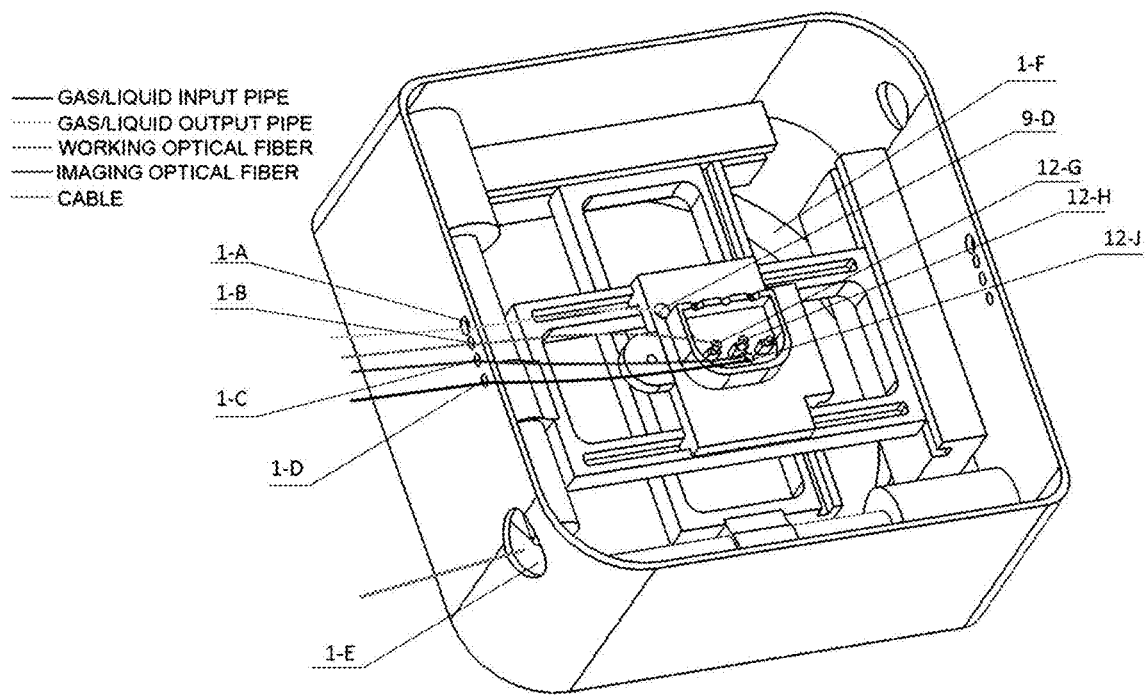
FIG. 11 schematically illustrates connection of the root canal treatment robot in accordance with an embodiment of the present application.

FIG. 10 shows the gas/liquid circuit unit of the root canal treatment robot system. FIG. 11 shows the line connection of the robot for the root canal treatment. In the root canal preparation, it is required to feed cold air for cooling and remove the dust generated in the cutting process. After the preparation, it is required to feed the relevant drugs for filling and disinfection. The gas/liquid circuit unit mainly includes a container for holding relevant drugs and a filling paste (Liquid 1, Liquid 2 and Liquid 3), a recycling container, electromagnetic valves (E1, E2, E3 and E4) for controlling the communication of each branch, and power pumps (Pump 1 and Pump 2) and a pipeline. The gas/liquid input pipe delivers the gas or the liquid into the pulp cavity or the root canal, and the gas/liquid output pipe transfers gas, dust and other substances from the pulp cavity and the root canal to the recycling container. The gas/liquid input pipe passes through the hole 1-D and the hole 12-J to reach the pulp cavity, and the gas/liquid output pipe passes through the hole 1-A and the hole 9-D to reach the pulp cavity. The working optical fiber 12-2 passes through the hole 1-B and the hole 12-G and extends out from the hole 9-A to reach the pulp cavity and the root canal, and the illuminating and imaging optical fiber 12-1 passes through the hole 1-C and the hole 12-H and extends out from the hole 9-A to reach the pulp cavity and the root canal orifice.

In the robot system provided herein, in addition to the traditional motor control, the movement can also be controlled by a thermodynamic, magnetic or pneumatic method, or a magnetic or dielectric elastomer artificial muscle.

The embodiment further provides a root canal treatment method, which is preferably implemented by the above-mentioned microrobot. It should be understood that this method can also be implemented with other root canal treatment apparatuses with xyza four-degrees-of-freedom motion and a controllable-bending working optical fiber.

The root canal treatment method provided herein will be described in detail below to clearly describe the differences and advantages with respect to the conventional treatment.

(S1) Determination of the Approach, Opening Position and Endodontic Access Cavity Traditionally, the opening position and endodontic access cavity are outlined in mind through the combination of visual observation and X-ray film.

In this embodiment:

(1) the three-dimensional data of the target tooth, the pulp cavity and root canal is obtained by cone beam computerized tomography (CBCT); and (2) the pulp hole design software is operated by the dentist to extract the pulp hole area from the three-dimensional data to obtain the 3D morphological data of the tooth hard tissue to be removed.

(S2) Penetration of the Pulp Cavity, Removal of the Roof of the Pulp Cavity, and Trimming of the Side Wall of the Pulp Cavity Regarding the traditional method, a high-speed turbine dental handpiece and a bur are held by a dentist to remove the hard tissue on the target tooth according to the position and shape of the cavity hole in mind, so as to form the endodontic access cavity. Then the dentin protruded on the wall of the pulp cavity is removed by visual observation or the reflection of the mouth mirror, so as to make each root canal orifice completely exposed.

In this embodiment:

(1) the tooth retainer is fixed on the target tooth and its adjacent teeth and tissues, and an intraoral part of the root canal treating microrobot is rigidly connected with the tooth retainer, so that the robot's coordinate system and the target tooth's coordinate system are kept in the same coordinate system;

(2) the motion path of the femtosecond laser spot is obtained with the help of the path planning software according to the three-dimensional data of the tooth hard tissue obtained in step (1);

(3) the intelligent recognition system automatically inputs the path planning data into the controlling software of the robot, and controls the x-axis and y-axis micro-motors to drive the hollow optical fiber to reach the initial position of the pulp opening, and the ends of the air supply and suction pipes also reach the corresponding position; the rolling wheel is controlled by the automatic controlling software to drive the hollow optical fiber to move up and down to complete the focusing; and according to the predetermined motion path, the tooth hard tissue above the pulp cavity is removed by the laser spot layer by layer to complete the pulp opening process; and (4) during the laser cutting of the tooth hard tissue, the air pump controlling software is operated to automatically control the delivery of cold air for cooling and suck out the dust generated by the cutting at the same time.

(S3) Positioning of the Root Canal Orifice

Traditionally, the root canal is explored and located using the DG-16 endodontic probe or other instruments.

In this embodiment:

(1) when the intelligent recognition system detects that the endodontic access cavity is consistent with the designed endodontic access cavity, the motion path of the outlet end of the Y-shaped channel will be planned by automatically operating the path planning software according to the three-dimensional data of the root canal orifice reconstructed in step (1); and (2) the planned data is automatically transferred to the robot controlling software to control the movement of the Y-shaped channel, such that the end of the Y-shaped channel reaches the vicinity of each root canal in turn.

(S4) the Root Canal is Explored and Negotiated to Establish a Root Canal Access, Measure the Length of the Root Canal and Complete the Root Canal Preparation, Forming a Negotiated Root Canal with a Continuous Tapered Inner Wall.

Traditionally, a small K-file is employed to negotiate the root canal, and then the length of the root canal is measured by a root canal measurement apparatus; and then different modes of root canal files are used to gradually expand the access.

In this embodiment:

(1) when the intelligent recognition system detects that the Y-shaped channel reaches the predetermined root canal orifice, the path planning software is automatically operated to plan the extension and bending of the optical fiber according to the three-dimensional data of the root canal reconstructed by CBCT;

(2) the path planning data is automatically transmitted to the controlling software of the robot, which issues instructions to control the rolling wheel in the robot to rotate, such that the illuminating and imaging optical fiber gradually extends; after reaching the designated position, the length and location of the illuminating and imaging optical fiber are recorded; then the illuminating and imaging optical fiber is retracted, and the femtosecond laser hollow optical fiber is driven to gradually extend;

(3) when the intelligent recognition system detects that the hollow optical fiber reaches the predetermined position, the air pump controlling software is called to automatically control the quantitative feeding of the hot air at a fixed temperature to the optical fiber, causing the quantitative deformation and bending of the deformable materials attached to the optical fiber (including temperature-based elastic materials, and other acoustic, optical, dielectric, thermal and magnetic materials, such as polyester polymers and titanium-nickel memory wire alloys);

(4) during the extension process of optical fiber, the femtosecond laser automatic control software is called to adjust the spot and power of the femtosecond laser in real time, so that it acts on the residue and inner wall of the root canal, and cuts the root canal according to the pre-planned path to prepare a continuous and unobstructed tapered root canal;

to arrive at the preset taper, the self-characteristic of the laser Gaussian beam or the additional controllable micro-radius oscillating device is used to control the fiber to move from top to bottom or from bottom to top, during the extension process of the working optical fiber into the root canal, thereby obtaining a continuous unobstructed tapered root canal according to the pre-planning, see Equation 1:

$$F(\varphi)=f(\omega,v) \quad (1);$$

where φ is the root canal taper, ω is the laser power, and v is the moving speed of the optical fiber; and (5) during the femtosecond laser cutting of the tooth tissue, the air pump control software is called to automatically control the air flow to suck out the dust generated by the cutting in time.

(S5) Irrigation and Disinfection of the Root Canal

Traditionally, a root canal irrigator is employed to sequentially take sodium hypochlorite, EDTA, chlorhexidine and normal saline to irrigate and disinfect the root canal, so as to remove the parasitic microorganisms in the root canal completely.

In this embodiment:

(1) when the intelligent recognition system detects that the tapered root canal is consistent with the predetermined design, the robot control software is automatically called to control the air inlet pipes to point to the individual root canals in sequence; and (2) the air pump controlling software is automatically called to open the valve of the medicine storage tank, quantitatively feed a irrigation and disinfection liquid, at a constant pressure, then control the suction tube to suck the liquid out, which are repeated for three to four times, and automatically control the input of hot air to dry the root canal and the pulp cavity.

(S6) Filling of the Root Canal

Warm Gutta-Percha filling is a traditional method. The prepared root canal sealer is applied to a thin layer with a paper twist on the root canal wall by the dentist, and an injection needle of a Gutta-Percha filling system is inserted into the root canal 3-5 mm distant to an apex of the root to inject the Gutta-Percha and then compact it.

In this embodiment:

(1) after the intelligent pattern recognition system detects that the pulp cavity and root canal are in a dry state, the path planning program is automatically called to form the planned data, which is input to the robot controlling software to control the air inlet to point to the position of each root canal orifice in turn; and (2) the air pump controlling software is automatically called to close the air intake tube, and open the suction tube to quantitatively form a negative pressure, open the valve of the root canal sealant storage tank and close the valves of the other storage tank, and suck the root canal sealant to the wall of the root canal. Then open the valve of the hot Gutta-Percha storage tank, under the action of the negative pressure, the hot Gutta-Percha is automatically introduced into each root canal to complete the filling process.

It should be noted that the above-mentioned intelligent recognition system is an optional software for the operation of the root canal treatment microrobot. The related operations implemented by the system can also be completed manually, so that the root canal treatment micro-robot can be used to achieve the semi-automatic root canal treatment.

Described above are merely preferred embodiments of the present application, which are not intended to limit the present application. It should be understood that various modifications, replacements and changes made by those skilled in the art without departing from the spirit of the application should still fall within the scope of the present application defined by the appended claims.

What is claimed is:

1. A robot for root canal treatment, comprising:
a main body;
an x-axis movement unit;
a y-axis movement unit;
a pan tilt;
a z-axis movement unit; and
an a-axis movement unit;
wherein the x-axis movement unit, the y-axis movement unit, the pan tilt, the z-axis movement unit and the a-axis movement unit are arranged inside the main body;
the pan tilt is in sliding fit with the x-axis movement unit and the y-axis movement unit, and is configured to be driven by the x-axis movement unit and the y-axis movement unit to move in an x-y plane;
the z-axis movement unit is arranged on the pan tilt, and is configured to drive an optical fiber for the root canal treatment to move along a z-axis; and the optical fiber penetrates through the pan tilt; and
the a-axis movement unit is arranged on the pan tilt, and is configured to drive the optical fiber to rotate around the z-axis;
the a-axis movement unit comprises an a-axis driving motor, a driving transmission friction wheel, an idler wheel and a driven transmission friction wheel; and
the driving transmission friction wheel is fixedly connected to a motor shaft of the a-axis driving motor; the idler wheel is in rotating fit with a first shaft provided at a bottom of the pan tilt; the driven transmission friction wheel is in rotating fit with a second shaft provided at the bottom of the pan tilt, so that a friction wheel transmission is formed by the driving transmission friction wheel, the idler wheel and the driven transmission friction wheel.

2. The robot of claim 1, wherein the optical fiber penetrates through the pan tilt along the z-axis, and a bending direction and a bending degree of the optical fiber are controllable.

3. The robot of claim 1, wherein at least one of the z-axis movement unit and the y-axis movement unit comprises a driving part, a transmission part and a guide part; the driving part comprises one of a motor drive system, a pneumatic drive system, an electric drive system, a hydraulic drive system, a gas-hydraulic hybrid drive system, an artificial muscle, and dielectric, magnetic, acoustic, optical, thermal and wind-based polymer, metal, and bio-elastomer drive systems; and the transmission part comprises one of a screw transmission part, a wire rope transmission part, a belt transmission part, a chain transmission part, and a gear transmission part.

4. The robot of claim 1, wherein the x-axis movement unit comprises an x-axis driving motor, an x-axis screw rod, an x-axis movable sliding rail and an x-axis movable sliding rod; and the y-axis movement unit comprises a y-axis driving motor, a y-axis screw rod, a y-axis movable sliding rail and a y-axis movable sliding rod;
the x-axis movable sliding rod is in fit with the x-axis screw rod through a first surface, and the y-axis movable sliding rod is in fit with the y-axis screw rod through a second surface;
the x-axis movable sliding rod is in fit with a chute of the x-axis movable sliding rail through a third surface, and the y-axis movable sliding rod is in fit with a chute of the y-axis movable sliding rail through a fourth surface; and
the pan tilt is in fit with a chute on the x-axis movable sliding rod through a fifth surface, and the pan tilt is in fit with a chute on the y-axis movable sliding rod through a sixth surface.

5. The robot of claim 1, wherein the z-axis movement unit comprises a z-axis driving motor, a z-axis screw rod, a z-axis movable sliding rail and a z-axis movable sliding rod, an upper platform, a first rolling wheel axle, a second rolling wheel axle, a driving transmission friction wheel, a permanent magnet, a driving optical fiber friction wheel, a first driven transmission friction wheel, a first electromagnetic coil, a first driven optical fiber friction wheel, a second driven transmission friction wheel, a second electromagnetic coil and a second driven optical fiber friction wheel;
the upper platform is fixedly connected to the pan tilt; and the z-axis driving motor is fixedly connected to the upper platform, and a motor shaft of the z-axis driving motor is in rotating fit with a first surface and a second surface of the upper platform;
the driving transmission friction wheel, the permanent magnet and the driving optical fiber friction wheel are fixedly connected to the motor shaft of the z-axis driving motor;
a third surface of the first rolling wheel axle is in rotating fit with a fourth surface of the upper platform, and is configured to slide on a fifth surface of the upper platform; the first driven transmission friction wheel, the first electromagnetic coil and the first driven optical fiber friction wheel are fixedly connected to a first wheel axle tube; the first wheel axle tube is in rotating fit with the first rolling wheel axle, and the first wheel axle tube and the first rolling wheel axle are capable of rotating relative to each other; the first wheel axle tube is restricted by a first snap spring or a first axle sleeve to move along an axial direction of the first rolling wheel axle; a sixth surface of the first rolling wheel axle is provided with a first torsion spring to separate the first rolling wheel axle from a z-axis driving shaft when the first electromagnetic coil is not energized; and
a seventh surface of the second rolling wheel axle is in rotating fit with an eighth surface of the upper platform, and is capable of sliding on a ninth surface of the upper platform; the second driven transmission friction wheel, the second electromagnetic coil and the second driven optical fiber friction wheel are fixedly connected to a second wheel axle tube; the second wheel axle tube is in rotating fit with the second rolling wheel axle, and the second wheel axle tube and the second rolling wheel axle are capable of rotating relative to each other; the second wheel axle tube is restricted by a second snap spring or a second axle sleeve to move along an axial direction of the second rolling wheel axle; and a tenth surface of the second rolling wheel axle is provided with a second torsion spring to separate the second rolling wheel axle from the z-axis driving shaft when the second electromagnetic coil is not energized.

6. The robot of claim 1, wherein the pan tilt further comprises a Y-shaped optical fiber channel; the Y-shaped optical fiber channel is provided at the bottom of the pan tilt, and comprises a first channel for the optical fiber for the root canal treatment and a second channel for an illuminating and imaging optical fiber; and
the first channel and the second channel share an outlet, and the second shaft is provided at the outlet.

7. The robot of claim 6, wherein the optical fiber for the root canal treatment passes through the first channel, and has a cross-section adapted to the outlet of the first channel in shape.

8. The robot of claim 7, wherein the cross-section of the optical fiber for the root canal treatment is non-circular, and the outlet of the first channel is non-circular to be adapted to the cross-section of the optical fiber for the root canal treatment.

9. The robot of claim 1, further comprising:
a gas/liquid circuit unit,
wherein the gas/liquid circuit unit comprises a container for holding a drug and a filling paste, a recycling container, a plurality of electromagnetic valves respectively for controlling communication of a plurality of individual branches, a power pump and a pipeline.

10. The robot of claim 1, further comprising:
a tooth retainer,
wherein the tooth retainer is configured to be fixed to a dentition of a patient and to fix the main body; and the tooth retainer is provided with a through hole to expose a surgical field.

11. A root canal treatment method using the robot of claim 1, comprising:
fixing the robot relative to a dental hard tissue, and initializing a position of an end of a working optical fiber of the robot according to a coordinate system of the dental hard tissue;
adjusting a height of the end of the working optical fiber relative to a target tooth to complete laser focusing of the working optical fiber; and
controlling the working optical fiber to move according to a first preset path, and removing the dental hard tissue above a pulp cavity of the target tooth layer by layer, so as to complete an opening of the pulp cavity of the target tooth.

12. The root canal treatment method of claim 11, further comprising:
during the step of removing the dental hard tissue of the body above the pulp cavity of the target tooth layer by layer, controlling the robot to deliver cold air to cool a surgical site through a delivery pipeline and to discharge dust generated in a cutting process from the surgical site through a discharge pipeline.

13. The root canal treatment method of claim 11, further comprising:
after the opening of the pulp cavity of the target tooth is completed, controlling the working optical fiber of the robot to move in accordance with a second preset path, such that the end of the working optical fiber reaches a vicinity of each root canal in sequence.

14. The root canal treatment method of claim 13, further comprising:
after the end of the working optical fiber reaches a vicinity of a root canal, controlling an illuminating and imaging optical fiber of the robot to move along a third preset path; and after the illuminating and imaging optical fiber reaches a designated position, recording a length and a position of the illuminating and imaging optical fiber and withdrawing the illuminating and imaging optical fiber;
controlling the working optical fiber of the robot to move to the designated position according to the recorded length and position of the illuminating and imaging optical fiber; controlling the working optical fiber to generate a controllable bending having the same bending direction and degree with the root canal, and controlling the working optical fiber toy extend into the root canal; and
cutting the root canal into a continuous and unobstructed tapered root canal according to a predetermined design during the process of extending the working optical fiber into the root canal.

15. The root canal treatment method of claim 14, further comprising:
during the step of cutting the root canal into a continuous and unobstructed tapered root canal according to a predetermined design, controlling the robot to discharge dust generated in the cutting process from a surgical site through a discharge pipeline.

16. The root canal treatment method of claim 13, further comprising:
after the end of the working optical fiber reaches a vicinity of a root canal, controlling the robot to quantitatively feed an irrigation and disinfection liquid to a surgical site at a constant pressure through a first delivery pipeline, and discharging the irrigation and disinfection liquid from the surgical site through a discharge pipeline; and
controlling the robot to deliver hot air to the surgical site through a second delivery pipeline to dry the root canal and the pulp cavity.

17. The root canal treatment method of claim 13, further comprising:
after the end of the working optical fiber reaches a vicinity of a root canal, controlling the robot to discharge air from the surgical site to outside through a discharge pipeline to quantitatively form a negative pressure such that a root canal sealant is sucked to a wall of the root canal through a delivery pipeline, and Gutta Percha is fed into the root canal through the delivery pipeline to complete filling of the root canal.

* * * * *